United States Patent [19]

Talley et al.

[11] Patent Number: 4,560,810

[45] Date of Patent: Dec. 24, 1985

[54] CATALYTIC DEALKYLATION OF ALKYLATED PHENOLS

[75] Inventors: John J. Talley, Clifton Park; Irene A. Evans, Schenectady; Michael D. Lewis, Albany, all of N.Y.

[73] Assignee: General Electric Company, Schenectady, N.Y.

[21] Appl. No.: 671,254

[22] Filed: Nov. 14, 1984

[51] Int. Cl.$^4$ .............................................. C07C 37/50
[52] U.S. Cl. .................................................... 568/805
[58] Field of Search ......................................... 568/805

[56] References Cited

U.S. PATENT DOCUMENTS 4,191,844  3/1980  Bjornson ............................ 568/805
4,230,895 10/1980  Daly .................................. 568/805
4,230,896 10/1980  Daly .................................. 568/805

FOREIGN PATENT DOCUMENTS 39525 12/1970  Japan ................................... 568/805

OTHER PUBLICATIONS

Daly, "J. Catalysis" vol. 61, p. 528 (1980).
Jelinck, "Chemical Abstracts" vol. 55, p. 7357 (1961).

*Primary Examiner*—Werren B. Lone
*Attorney, Agent, or Firm*—William H. Pittman; James C. Davis, Jr.; James Magee, Jr.

[57] ABSTRACT

Alkylated hydroxyaromatic compounds, particularly alkylated phenols such as mesitol and 2,4-xylenol, are selectively ortho-dealkylated by contact at a temperature within the range of about 350°–500° C. with a catalyst comprising a combination of at least one chromium oxide and at least one of the oxides of zinc, iron, magnesium and manganese, with zinc and iron being preferred.

12 Claims, No Drawings

CATALYTIC DEALKYLATION OF ALKYLATED PHENOLS

This invention relates to a method for dealkylating alkylated hydroxyaromatic compounds. More particularly, this invention is directed to a method for dealkylating ortho- and para-alkylated phenols with steam in the presence of a mixed metallic oxide catalyst.

It is often desirable to dealkylate hydroxyaromatic compounds, especially the alkylated phenols obtained from coal tars from coal liquefaction processes, to provide more valuable products, such as phenol. In addition, it is often desirable to dealkylate 2,4,6-trimethylphenol (TMP), a coproduct in the synthesis of 2,6-xylenol, to more useful alkylated phenols. Especially desirable as products are the para-alkylated phenols such as p-cresol and 2,4-xylenol.

Methods of dealkylating alkylated hydroxyaromatic compounds are known in the art. These methods include thermal dealkylation, thermal hydrodealkylation and catalytic hydrodealkylation. Thermal dealkylation involves the exposing the alkylated hydroxyaromatic compounds to high temperatures (about 800° C.) to achieve thermal cracking thereof. However, this process is not selective and a substantial amount of dehydroxylation occurs under these conditions, producing the less valuable hydrocarbon species, as is shown more particularly by Daly in *Journal of Catalysis*, 61, 528 (1980), the contents of which are incorporated herein by reference.

Thermal hydrodealkylation of alkylated hydroxyaromatic compounds involves exposing them to high temperatures in the presence of steam or hydrogen or both, as is shown by Daly in U.S. Pat. No. 4,230,895. This process also causes a significant amount of dehydroxylation.

Catalytic hydrodealkylation is typically more selective than the processes described above and causes less dehydroxylation. Daly describes a process in U.S. Pat. No. 4,230,896 wherein alkylated hydroxyaromatic compounds are reacted with steam in the presence of a catalyst comprised of a hydrous carrier, a deactivation suppressor and at least one promoter. Catalysts included within those described by Daly include platinum and palladium on alumina and mixtures of palladium and chromium oxide on alumina. A catalytic hydrodealkylation process which reacts alkylated hydroxyaromatic compounds with hydrogen is described by Bjornson in U.S. Pat. No. 4,191,844. This reaction takes place in the presence of a catalyst consisting essentially of manganese oxide and a Group IIA metal oxide such as magnesium oxide. Although these catalytic hydrodealkylation processes are more selective and cause less dehydroxylation than thermal hydrodealkylation, there still remains room for improvement. For example, the percent conversion of reactant is very low (about 40%) in the process described in U.S. Pat. No. 4,230,896 and dehydroxylation is still significant providing 5-30% (by weight) dehydroxylated products. In the process described by Bjornson, the rate of dehydroxylation is also high, producing large quantities of dehydroxylated products (up to 50%) at high rates of dealkylation. In addition, these processes which utilize a catalyst are handicapped by the short lifetime of the catalyst due to coking. The catalyst must be reactivated or regenerated periodically and a deactivation suppressant is often necessary.

An object of the present invention, therefore, is to dealkylate alkylated hydroxyaromatic compounds with substantially no loss of hydroxyl radicals.

Another object is to dealkylate alkylated hydroxyaromatic compounds at a high conversion rate, using a catalyst with a long lifetime and high selectivity for ortho-dealkylation.

Other objects will in part be obvious and will in part appear hereinafter.

In its broadest sense, the present invention is directed to a method of dealkylating alkylated hydroxyaromatic compounds containing at least one alkyl group ortho to the hydroxy group which comprises contacting, at a temperature within the range of about 350°-500° C., a combination of at least one such alkylated hydroxyaromatic compound and water with a catalyst comprising a combination of at least one chromium oxide and at least one of the oxides of zinc, iron, magnesium and manganese.

The present invention is directed to a catalytic steam dealkylation process which selectively dealkylates the positions ortho to the hydroxyl radical of an alkylated hydroxyaromatic compound. The term "dealkylation" as used herein refers to the removal from the aromatic nucleus of alkyl groups containing about 1-6 carbon atoms. The term "dehydroxylation" refers to the loss of the hydroxyl radical on the aromatic nucleus. The method of this invention dealkylates alkylated phenols with a high degree of ortho-selectively and essentially no dehydroxylation.

Suitable alkylated hydroxyaromatic compounds which can be dealkylated by this process include those containing one hydroxyl radical and at least one alkyl group at an ortho- or para-position relative to said hydroxyl radical. These compounds may contain multiple alkyl groups which may be straight chain or branched. Examples of suitable alkylated phenols include o-cresol, 2,4-xylenol, 2,3-xylenol, 2,5-xylenol, 2,6-xylenol, 2,3,4-trimethylphenol, 2,3,5-trimethylphenol, 2,3,6-trimethylphenol, 2,4,6-trimethylphenol (mesitol), 2,4,5-trimethylphenol, 3,4,5-trimethylphenol, 2-ethylphenol, 4-ethylphenol, 2,4-diethylphenol, 2-isopropylphenol, 2-methyl-1-naphthol and 3-methyl-2-naphthol. The monocyclic compounds are preferred; especially preferred are mesitol and 2,4-xylenol. Mixtures of alkylated hydroxyaromatic compounds, including those derived from tar acids obtained from coal liquefaction processes, may also be dealkylated. For brevity, the term "alkylated phenol" is frequently used hereinafter since alkylated phenols are preferred; however, it should be understood that other alkylated hydroxyaromatic compounds may be used in place thereof.

According to the present invention, dealkylation is effected in the presence of a catalyst which is a combination of at least one chromium oxide and at least one of the oxides of zinc, iron, magnesium and manganese. Zinc and iron are preferred, with iron being especially preferred because of its relatively long life before regeneration is necessary and its low tendency to effect disproportionation forming more highly alkylated phenols as by-products. In general, chromium oxide is present in minor proportion (i.e., less than 50 mole percent); it usually comprises about 0.5-25 mole percent.

A number of suitable catalysts are commercially available. They include, for example, "Zn-0312T" sold by Harshaw Chemical Company, which comprises 74 mole percent zinc oxide and 21 mole percent chromic oxide, and "UCI-G3" of United Catalysts Inc., which comprises 91 mole percent ferric oxide and 9 mole percent chromic oxide. It is also possible to prepare a suitable catalyst by coprecipitation of the metal oxides from an alkaline aqueous medium free from other metal ions. For this purpose, the chromium oxide used may be either $Cr_2O_3$ or $CrO_3$, since the hexavalent oxide will be reduced to the trivalent oxide under dealkylation conditions by hydrogen, which is formed along with carbon dioxide as a by-product. The use of trivalent chromium is preferred because of its decreased tendency to form tars and coke and to produce a dark product.

As a general rule, catalyst activity increases with an increase in surface area. Calcination of the catalyst used according to this invention usually increases substantially the surface area thereof. Such calcination is typically accomplished at a temperature within the range of about 400°–500° C. in the presence of an oxidizing gas such as air or oxygen. Suppression of coke formation is also desirable, since coke deposits on the catalyst and decreases its surface area. Optimum dealkylation results are usually obtained when the surface area of the catalyst is at least about 25 $m.^2/g$.

The catalyst is generally employed in the form of pellets. Optimum pellet diameter is typically ⅛ inch (about 3.2 mm.).

The catalyst may contain an inert organic or inorganic binder to facilitate pelletization and increase ease of handling. Suitable binders include polyphenylene oxide and graphite. Surface area-increasing components such as silica, titania and germanium dioxide may also be present. Such binders and surface area-increasing components comprise up to a total of about 20% (by weight) of the catalyst.

The preparation of a catalyst suitable for use in the method of this invention is illustrated by the following example.

EXAMPLE 1

To a solution in 400 ml. of deionized water of 300 grams (0.742 mole) of ferric nitrate nonahydrate and 2.97 grams (0.0074 mole) of chromic nitrate nonahydrate was added 100 ml. of an 11% (by weight) silica aquasol to serve as a binder. The mixture was stirred at room temperature as concentrated ammonium hydroxide was added dropwise to a pH of 7.0. Vigorous stirring was continued for 1 hour and additional ammonium hydroxide was added dropwise to a final pH of 10. Acetone, 500 ml., was added and the precipitated iron-chromium mixture was removed by filtration, dried 180° C./20 Torr for 10 hours, crushed, passed through a sieve and calcined in air at 470° C. for 4 hours. The surface area of the calcined catalyst was 85.61 $m.^2/g$.

The method of this invention can be carried out in conventional reactors used for vapor phase reactions over a solid catalyst. For example, a tubular reactor of quartz or metal filled with a static catalyst bed is suitable. The reactor may be heated by any conventional means; for example, by surrounding the reactor with an electric heater or a heated gas or liquid. Multiple electric heaters with separate controls frequently permit easy control of the catalyst bed temperature.

The alkylated phenols are preferably in the vapor phase when in the presence of the catalyst at the operable temperature ranges. To avoid cooling of the catalyst below the reaction temperature selected, it is preferable to vaporize and preheat the starting materials prior to contact with the catalyst. To minimize the decomposition of the starting materials, they may be maintained at the minimum temperature necessary for vaporization and then preheated to the desired reaction temperature immediately prior to contact with the catalyst. This can be accomplished by passing the vaporized starting materials through a heated tube of metal or quartz over heated quartz beads just prior to entry into the catalyst bed. It is preferable to utilize the same heating medium to preheat the vapors which is used to heat the catalyst bed so as to maintain a consistent reaction temperature.

It is within the scope of the invention to dissolve the alkylated phenols in an organic solvent which is inert under dealkylation conditions, although a solvent is not generally necessary, especially if the alkylated phenols are liquids. Suitable solvents include alkanes such as hexane, aromatic hydrocarbons such as benzene, halogenated aromatic hydrocarbons such as chlorobenzene, and ethers such as tetrahydrofuran.

The dealkylation reaction proceeds at a temperature within the range of about 350°–500° C. with relatively little dehydroxylation, with temperatures within the range of 380°–400° C. frequently being preferred. At such temperatures, the alkylated phenols in the feed and the dealkylated phenols produced are in vapor form.

The reaction proceeds smoothly at atmospheric pressure, which makes it convenient to carry out the process since complex equipment is not required and the hazards which are characteristic of reactions which proceed under pressure avoided. However, pressures above and below atmospheric pressure can be utilized when desired. The pressure is preferably maintained within the range of about 1–50 atmospheres, with pressure at about one atmosphere being the most preferred. The temperature ranges can vary if the reaction takes place at a pressure other than at one atmosphere.

The rate (liquid hourly space velocity or LHSV) at which alkylated phenols and water (which is present as steam under the reaction conditions) are contacted with the catalyst is not critical. The flow rate of reactant does affect the product yield by determining the amount of contact time between the alkylated phenols, water and catalyst. Due to the difference in the specific activities of various catalysts, each catalyst will have a different optimum flow rate. The more active the catalyst, the shorter the contact time necessary to produce the same quantity of dealkylated phenols. Therefore, to obtain a particular conversion rate, higher LHSV's can be used with more active catalysts while lower LHSV's are necessary with less active catalysts. A flow rate which is too high will flood the catalyst and inhibit the reaction. An alkylated phenol LHSV in the range of about 0.1–3.0 grams per hour per gram of catalyst is preferred. The most preferred LHSV is about 0.3–0.5 grams per hour per gram of catalyst. The water LHSV is typically substantially equal that of the alkylated phenol; for example, about 80–120% thereof.

It is frequently advantageous to employ a gaseous carrier for the alkylated phenol and water. Suitable carriers include inert gases such as nitrogen or argon and oxidizing gases such as oxygen and air. Unlike certain other catalysts, however, those used in the method of this invention do not require contact with an oxidizing atmosphere or carrier gas.

The reactor effluent comprises products and unreacted starting materials, together with any solvent used. It normally exits the catalyst bed in vapor form and may be condensed to liquid by conventional means, such as condensation using air or water condensers. The components of the effluent may then be separated by distillation or the like.

The catalysts employed according to this invention can be used in the dealkylation process for long periods of time, typically several hundred hours, before substantial loss in activity occurs. When such loss is noted, the catalyst may be regenerated by heating in the presence of water and an oxygen-containing gas, typically air. A principal effect of such heating is to remove coke and related deposits from the catalyst surface by oxidation. Such oxidation typically begins when the temperature of the system is at least 300° C. The oxidation reaction is exothermic and the temperature is preferably maintained below about 450° C. during the initial stage of the regeneration process, typically by regulating the flow of oxygen-containing gas. When removal of deposits is substantially complete, the temperature may be raised to calcination level for the final part of the regeneration process.

The method of this invention is illustrated by a series of experiments in which the apparatus consisted of a reactor tube containing 60–120 ml. of catalyst and a coiled preheater tube, packed with quartz chips in some experiments. The system was maintained at a temperature within 10 degrees of the indicated reaction temperature by means of a fluidized sand bath or thermocouple-controlled heating tape. The alkylated phenol and water were metered into the reactor at identical LHSV's and the internal back pressure was maintained at 0–50 psi. The reactor effluent was cooled and separated into organic and aqueous phases, and the organic phase was analyzed by gas chromatography.

In the tables, times are in hours, LHSV's (for either component individually) are in grams per hour per gram of catalyst, temperatures are in degrees Centigrade and product composition figures are in percent by weight.

EXAMPLES 2–8

The catalyst was "UCI-G3", and the gas flow rate was 0.4 SCFH (standard cubic feet per hour). The alkylated phenol was 2,4-xylenol. The gas used was air in Examples 1–3 and nitrogen in Examples 4–7. In Example 4 the same catalyst batch was used for two successive runs under listed conditions. The results are given in Table I.

TABLE 1

|  | 2 | 3 | 4 | 5 | 6 | 7 | 8 |
|---|---|---|---|---|---|---|---|
| Time, hrs. | 1 | 7 | 1.33 | 2.75 | 1 | 3 | 2.5 | 6 |
| LHSV | 0.12 | 0.24 | 1 | 0.25 | 0.12 | 0.35 | 0.35 | 0.15 |
| Temperature | 380 | 400 | 400 | 400 | 400 | 350 | 375 | 400 |
| Product composition: | | | | | | | | |
| 2,4-Xylenol | 20.96 | 87.45 | 53.65 | 62.98 | 52.73 | 65.29 | 64.22 | 38.64 |
| 2,6-Xylenol | — | 0.242 | — | — | — | — | 0.119 | — |
| Mesitol | — | 7.063 | 5.508 | 5.381 | 7.058 | 6.446 | 4.113 | 3.614 |
| p-Cresol | 37.25 | 9.787 | 27.84 | 27.43 | 33.7 | 22.41 | 23.9 | 40.23 |
| o-Cresol | — | 0.454 | 13.01 | 1.321 | 1.429 | 1.122 | 0.981 | 2.451 |
| Phenol | 10.98 | — | — | 1.252 | 1.942 | 1.443 | 1.76 | 7.26 |
| Hydrocarbons | 4.268 | — | — | — | 1.977 | 1.126 | 2.447 | 7.794 |

EXAMPLES 9–10

The procedure of Examples 2–8 was repeated, using in Example 9 the catalyst of Example 1 and in Example 10 a similarly prepared catalyst containing 95 mole percent ferric oxide and 5 mole percent chromic oxide. The gas used was nitrogen, and the temperature in both examples was 400° C. The results are given in Table II.

TABLE II

|  | Example 9 | Example 10 |
|---|---|---|
| Time, hrs. | 2 | 1 |
| LHSV | 0.38 | 1 |
| Product composition: | | |
| 2,4-Xylenol | 91.41 | 92.15 |
| 2,6-Xylenol | 0.016 | 0.52 |
| Mesitol | 2.364 | 2.39 |
| p-Cresol | 4.496 | 4.28 |
| o-Cresol | 0.311 | 0.68 |
| Phenol | 0.095 | — |
| Hydrocarbons | 0.061 | — |

EXAMPLE 11

The procedure of Examples 2–8 was repeated, except that the alkylated phenol was 2-ethylphenol. The gas was nitrogen, the temperature was 400° C., and the LHSV was 0.30. After 10 minutes, the product composition was as follows:

| 2-Ethylphenol | 84.15% |
|---|---|
| Mesitol | 0.235% |
| p-Cresol | 0.782% |
| o-Cresol | 1.08% |
| Phenol | 13.66% |
| Hydrocarbons | 0.098%. |

EXAMPLES 12–14

The procedure of 2–8 was repeated, using "Zn-0312T" as the catalyst and 2,4-xylenol as the alkylated phenol. In all examples, the temperature was 400° C. In Example 14, the conditions were changed periodically as indicated. The results are given in Table III.

TABLE III

|  | Example 12 | Example 13 | Example 14 | | | | |
|---|---|---|---|---|---|---|---|
| Time, hrs. | 3.25 | 5.75 | 3.25 | 6 | 2 | 4 | 7 |
| LHSV | 0.25 | 0.25 | 0.25 | 0.25 | 0.125 | 0.25 | 0.25 |
| Product composition: | | | | | | | |
| 2,4-Xylenol | 54.03 | 69.34 | 75.73 | 74.02 | 36.47 | 59.97 | 55.25 |
| Mesitol | 1.821 | 1.979 | 8.873 | 8.993 | — | 2.44 | 2.553 |
| p-Cresol | 37.02 | 24.88 | 14.63 | 15.73 | 53.23 | 32.91 | 37.27 |
| o-Cresol | 2.055 | 1.364 | 0.777 | 0.859 | 2.247 | 1.694 | 1.851 |
| Phenol | 5.066 | 2.424 | — | 0.245 | 8.046 | 2.983 | 3.076 |

EXAMPLE 15

The procedure of Examples 12–14 was repeated, using mesitol as the alkylated phenol and an LHSV of 0.25. After 1 hour, the product composition was as follows:

| 2,4-Xylenol | 28.52% |
|---|---|
| 2,6-Xylenol | 0.744% |
| Mesitol | 65.28% |
| p-Cresol | 4.216% |
| Phenol | 0.558%. |

EXAMPLE 16

The procedure of Example 15 was repeated, except that the system was maintained at a pressure of 25 psig.

and passage of gas was discontinued. The LHSV was 0.5 and the temperature was 408° C. After 600 hours, the product had the following composition:

| | |
|---|---|
| 2,4-Xylenol | 32.54% |
| 2,6-Xylenol | 2.40% |
| Mesitol | 49.97% |
| p-Cresol | 9.24% |
| o-Cresol | 4.34% |
| Phenol | 1.51%. |

What is claimed is:

1. A method of dealkylating alkylated phenols containing at least one alkyl group ortho to the hydroxy group which comprises contacting, at a temperature within the range of about 350°–500° C., a combination of at least one such alkylated phenol and water with a catalyst comprising a combination of at least one chromium oxide and at least one of the oxides of zinc, iron, magnesium and manganese.

2. A method according to claim 1 wherein the catalyst is a combination of chromic oxide and at least one of the oxides of zinc and iron.

3. A method according to claim 2 wherein the chromium oxide comprises about 0.5–25 mole percent of the catalyst.

4. A method according to claim 3 wherein the catalyst has been calcined at a temperature within the range of about 400°–500° C. in the presence of of an oxidizing gas.

5. A method according to claim 4 wherein the liquid hourly space velocity at which the alkylated phenol is contacted with the catalyst is about 0.1–3.0 grams per hour per gram of catalyst, and the water LHSV is about 80–120% of that of the alkylated phenol.

6. A method according to claim 5 wherein the alkylated phenol and water are preheated prior to contact with the catalyst.

7. A method according to claim 6 wherein the catalyst contains at least one material selected from the group consisting of inert organic and inorganic binders and surface area-increasing components.

8. A method according to claim 7 wherein the alkylated phenol is mesitol, 2,4-xylenol or a mixture thereof.

9. A method according to claim 8 wherein the catalyst is a combination of said chromium oxide and zinc oxide.

10. A method according to claim 9 wherein the dealkylation temperature is within the range of 380°–400° C.

11. A method according to claim 8 wherein the wherein the catalyst is a combination of said chromium oxide and iron oxide.

12. A method according to claim 11 wherein the dealkylation temperature is within the range of 380°–400° C.

* * * * *